US005635609A

United States Patent [19]
Levy et al.

[11] Patent Number: 5,635,609
[45] Date of Patent: Jun. 3, 1997

[54] PARTICLES PREPARED BY TRANSACYLATION REACTION BETWEEN AN ESTERIFIED POLYSACCHARIDE AND A POLYAMINE, METHODS OF PREPARATION THEREFOR AND COMPOSITIONS CONTAINING SAME

[75] Inventors: Marie-Christine Levy; Florence Edwards-Levy, both of Reims; Isabelle Orly, Lyons, all of France

[73] Assignee: Coletica, Lyons, France

[21] Appl. No.: 492,057

[22] PCT Filed: Apr. 13, 1994

[86] PCT No.: PCT/FR94/00409

§ 371 Date: Jul. 20, 1995

§ 102(e) Date: Jul. 20, 1995

[87] PCT Pub. No.: WO94/23832

PCT Pub. Date: Oct. 27, 1994

[30] Foreign Application Priority Data

Apr. 13, 1993 [FR] France ................... 93 04332

[51] Int. Cl.⁶ ........................................... B01J 13/14
[52] U.S. Cl. ................... 536/2; 536/3; 536/18.7; 536/20; 536/58; 536/63; 536/107; 536/110; 536/115; 536/119; 536/123.1; 424/489; 424/490; 424/491; 424/492; 424/493; 424/494; 424/495; 424/496; 424/497; 424/499; 424/501; 427/212; 427/213.3; 427/213.31; 427/213.32; 427/213.33; 427/213.35; 427/213.36; 264/4.1; 264/4.3; 264/4.33; 264/4.7

[58] Field of Search ............ 536/2, 3, 20, 18.7, 536/58, 63, 107, 110, 115, 119, 123.1; 424/489, 490, 491, 492, 493, 494, 495, 496, 497, 499, 501; 427/212, 213.3, 213.31, 213.32, 213.33, 213.35, 213.36; 264/4.1, 4.3, 4.32, 4.33, 4.7

[56] References Cited

U.S. PATENT DOCUMENTS

| | | | |
|---|---|---|---|
| 3,503,769 | 3/1970 | McDowell | 106/208 |
| 4,352,883 | 10/1982 | Lim | 435/178 |
| 5,132,242 | 7/1992 | Cheung | 436/501 |
| 5,194,300 | 3/1993 | Cheung | 427/213.31 |
| 5,298,410 | 3/1994 | Phillips et al. | 435/188 |

FOREIGN PATENT DOCUMENTS 2 145 992  4/1985  United Kingdom.

*Primary Examiner*—Nathan M. Nutter
*Attorney, Agent, or Firm*—Millen, White, Zelano, & Branigan, P.C.

[57] ABSTRACT

Particles, preparation methods therefor, and compositions containing same. The particles include at least one esterified polysaccharide and at least one polyamine, as well as at least one gellable polysaccharide when neither the esterified polysaccharide nor the polyamine can be gelled under the selected operating conditions. Said particle includes, at least on its surface, a membrane consisting of the product of the transacylation reaction between the esterified polysaccharide and said polyamine within an optionally gellable gel, said reaction causing the formation of covalent amide bonds. Such particles may be used to encapsulated various active principles useful in the fields of cosmetics, pharmaceuticals and agri-foodstuffs, enzymes, cells and micro-organisms.

49 Claims, 3 Drawing Sheets

ASSAY OF THE FREE ALKALINE PHOSPHATASE

ASSAY OF THE ENCAPSULATED ALKALINE PHOSPHATASE

PARTICLES PREPARED BY TRANSACYLATION REACTION BETWEEN AN ESTERIFIED POLYSACCHARIDE AND A POLYAMINE, METHODS OF PREPARATION THEREFOR AND COMPOSITIONS CONTAINING SAME

The present invention relates essentially to the use of a transacylation reaction with formation of covalent amide bonds between an esterified polysaccharide and a polyamine to form a stable membrane, in aqueous medium, at least at the surface of gelled particles, to the particles thus produced, to processes for their manufacture and to the compositions containing them.

More precisely, the present invention essentially relates to the use of a transacylation reaction between, on the one hand, a polysaccharide bearing esterified carboxylic groups, and, on the other hand, a polyamine, in order to form, in aqueous medium, a stable membrane at least at the surface of gelled particles, to the modified particles thus produced, to the processes used to form such modified particles, and to compositions containing the particles thus obtained, such as cosmetic, pharmaceutical, therapeutic, agrifood, enzymatic, biotechnological, reagent or diagnostic compositions.

TECHNOLOGICAL BACKGROUND

It is well known that spheres may be prepared very readily, for example from sodium alginate, by using the property of alginate solutions to gel in the presence of cations such as, for example, calcium ions. The material to be encapsulated in the spheres is first dispersed in the aqueous alginate solution. This solution is added dropwise to an aqueous solution of a calcium salt. There is immediate gelation, which produces spheres of gelled alginate. The surface of the spheres may then be stabilized by immersion in a solution of a polycationic polymer such as poly-L-lysine or polyethyleneimine (Lim, F., U.S. Pat. No. 4,352,883, 1982). A membrane forms at the periphery, resulting from ionic association between the alginate and the polycation. This membrane allows small molecules to pass through while retaining large molecules and cells. It is then possible to liquefy the inner gel by immersing the alginate spheres, stabilized by the polycationic polymer, in a citrate solution, so as to chelate the calcium in the spheres (Lim, F., U.S. Pat. No. 4,352,883, 1982). The material incorporated then remains contained within the membrane.

This process has the great advantage of being carried out entirely in aqueous medium and of retaining excellent viability with respect to encapsulated living cells, which may multiply within the capsule. Hence, it is widely used for the inclusion of living tissues, cells and microorganisms. Thus, alginate spheres containing microorganisms are used in the food industry in order to carry out fermentations (fermentation of dairy products, beer, champagne, etc.). These techniques are applied to plant or animal cells or organs with the aim of cryoprotecting or producing metabolites, to animal cells or tissues (islets of Langerhans, hepatocytes, etc.) for implantation in human or veterinary medicine (cell therapy), or for carrying out toxicology tests in vitro. Cells are also cultured in such spheres for the production of biological substances such as the monoclonal antibodies developed by hybridomas, which accumulate in the spheres and are thus easily harvested after opening the membranes.

However, the process has drawbacks associated with the nature of the membrane. As it involves no covalent bonds but only ionic bonds between the alginate and a polycation, it is of limited stability (Dupuy et al., J. Biomed. Mat. Res., 1988, 22, 1061–1070). The polymers have a tendency to pass into solution over time. Moreover, if the pressure increases within the capsule under the effect of cell multiplication, the membrane cannot resist the pressure and cells are released into the medium. It is thus often necessary to apply successively alternate layers of alginate and then of polycation ("sandwiches") in order to obtain a solid membrane which does not allow the contents to diffuse out (Wong H. and Chang T. M. S. Biomat. Art. Cells & Immob. Biotech., 1991, 19, 675–686).

French Application Document No. 9,210,173 (1992) describes the use of a transacylation reaction between a polysaccharide ester, such as propylene glycol alginate (PGA), and a polyamine substance, such as a diamine or a protein, in order to manufacture microcapsules. The transacylation reaction between the ester and the polyamine is triggered in alkaline medium and produces a membrane formed of a polysaccharide associated with a polyamine by amide bonds. This document describes several processes for the preparation of microcapsules, all using a step of emulsification, during which either an aqueous phase is dispersed in a hydrophobic phase or a hydrophobic phase is dispersed in an aqueous phase. In all cases, the microcapsules become individualized from the initial emulsion, by basification of the emulsion.

If an attempt is made to apply this transacylation reaction directly to an aqueous suspension of spheres formed of a polysaccharide gelling in gelled form by a gelling agent such as a mono- or polyvalent cation, generation of a membrane around the spheres is not achieved. Thus, for example, if spheres are prepared by dropwise addition of a sodium alginate solution to an aqueous calcium solution, if the said spheres are then dispersed in an aqueous solution containing an esterified polysaccharide, such as propylene glycol alginate, and a protein, and if finally the aqueous suspension is basified so as to trigger the transacylation reaction between the esterified polysaccharide and the protein, the aqueous solution visibly sets in bulk as soon as the pH is sufficiently high to allow the reaction to take place.

SUMMARY OF THE INVENTION

The aim of the present invention is to generate, in aqueous medium, a stable membrane, involving covalent bonds, at least at the surface of individualized spheres by gelation of a polysaccharide or of a polyamine in particular by a mono- or polyvalent cation such as, for example, a calcium salt.

Another aim of the present invention is to prepare stable particles, from polyamines and in particular proteins, at laboratory temperature, in aqueous medium, without a bifunctional crosslinking agent, and either containing a water-soluble substance, or containing a foam of air bubbles, or containing a water-insoluble substance, or containing living material such as animal or plant cells, tissues or organs, or seeds or eggs, or microorganisms, or containing a hydrophobic phase, depending on whether a solution, or a foam, or a suspension, or an emulsion will be prepared at the start in the initial gellable solution.

Another aim of the present invention is to prepare stable particles, from proteins, by limiting the changes in their structure, so as to obtain improved biocompatibility, and in the case where the protein is endowed with specific biological activity, so as to preserve this activity.

Another aim of the present invention is to prepare particles containing living materials by controlling the viability of the materials encapsulated, The aim of the present invention is to use the transacylation reaction between an esterified polysaccharide and a polyamine in order to manufacture spherical particles surrounded by a membrane, in strictly aqueous medium.

Another aim of the present invention is to apply the transacylation reaction between an esterified polysaccharide and a polyamine to spheres formed of a gelling polysaccharide or of a gelling polyamine in gelled form by a gelling agent such as a mono- or polyvalent cation, or a polyphosphate, or a solution of pH >6.2 depending on the nature of the gelling compound, so as to provide either spheres with an outer membrane and gelled contents, or spheres with an outer membrane and liquid contents, or spheres consisting of a gel which is stiffened throughout its bulk.

Another aim of the present invention is to overcome the technical problems listed above, with the use of simple manufacturing processes, which may be used on the industrial scale and make it possible moreover to control the size of the particles, in particular within a size range of from a few micrometers to 10 millimeters.

DETAILED DESCRIPTION OF THE INVENTION

According to the present invention, it has been discovered, entirely unexpectedly, that the creation of a stable membrane involving covalent bonds, at least at the surface of spheres formed of a gelling polysaccharide or of a gelling polyamine in gelled form by a gelling agent, could be achieved in an extremely simple manner, for example by dissolving an esterified polysaccharide and a polyamine in the initial solution of a gelling polysaccharide such as sodium alginate. The solution obtained is added in drop form to a gelling bath such as, for example, a solution of a calcium salt, so as to individualize the particles by gelation. The particles are washed with water and then redispersed in water. It then suffices to basify the aqueous suspension in order to trigger immediately the transacylation reaction between the esterified polysaccharide and the polyamine which are incorporated with the spheres. It is also possible to disperse the spheres directly in an alkaline aqueous solution, or alternatively to basify directly the gelling bath after formation of the gelled particles. It is then observed that a membrane forms at least at the periphery of the spheres. After reaction, the suspension is neutralized using an acid and the particles are washed with water. Spheres formed of the gelling polysaccharide in gelled form, which spheres are surrounded at least at the surface by a membrane consisting of a polyamine directly associated via amide bonds with the polysaccharide bearing initially-esterified carboxyls, are thus obtained.

It has also been discovered that a stable membrane could be created at least at the surface of spheres formed of the gelling polysaccharide in gelled form, for example formed of alginate gelled with a polyvalent cation such as, for example, a calcium salt, by incorporating only the esterified polysaccharide into the initial solution of the gelling polysaccharide. The spheres are individualized by gelation, for example on contact with a calcium salt, and are washed and then dispersed in an aqueous solution containing the polyamine. The reaction is then triggered by basifying the suspension. It is also possible to disperse the spheres directly in an alkaline aqueous solution of the polyamine, or alternatively to add the alkaline solution of polyamine directly to the gelling bath. After reaction, the suspension is neutralized by addition of an acid.

In a variant, the above procedure is applied by incorporating the polyamine both into the initial gellable aqueous phase and into the external phase to be basified. This thus compensates for the possible losses of polyamine by diffusion out of the particles or beads in aqueous medium.

It has also been discovered that, in the case where the esterified polysaccharide is itself capable of gelling in the presence of cations, as is the case, for example, for propylene glycol alginate or pectins in contact with calcium salts, it is then possible not to add gelling polysaccharide to the initial aqueous solution to be gelled containing the polyamine and the esterified polysaccharide. The esterified polysaccharide is then employed at higher concentrations so as to be able to play a double role in this variant: to ensure formation of the spheres by gelation, on the one hand, and to intervene in the subsequent formation of the membrane by transacylation during the subsequent basification of the suspension of spheres, on the other hand.

It has also been discovered that the gelled contents of the particles thus surrounded by a membrane according to the above principles could be liquefied by immersion in a citrate or phosphate solution. After rinsing the particles, spheres are obtained whose perfectly visible membrane traps a liquid content.

Finally, it has been discovered that, in these systems, the thickness of the membrane, its biodegradability and the narrowness of its pores could readily be controlled by varying the duration of the transacylation reaction and/or by varying the conditions of basification of the aqueous phase during the transacylation step. The membrane is proportionally thicker, and proportionally less sensitive to protease lysis and has proportionally narrower pores the longer the reaction lasts and/or the larger the amount of alkaline agent added to the aqueous suspension of spheres to be coated, or added to the aqueous phase used for their dispersion, or alternatively added to the gelling bath. The amounts of acid to be added are then also increased, so as to allow the suspension to be neutralized. If the basification is performed with even higher amounts of alkaline agent and/or with even longer reaction times, the transacylation reaction then concerns the entire bulk of the sphere whose content is thus stiffened and retains its solid consistency even after treatment with sodium citrate.

It is on the basis of this discovery, which is entirely unexpected for those skilled in the art, that the present invention has been produced.

The invention represents progress which is decisive for those skilled in the art, given that the membranes of the spherules obtained result from the establishment of covalent amide bonds, by the transacylation reaction. They are thus perfectly stable. Furthermore, their constitution involves only biocompatible substances. They may thus find numerous applications in various fields, such as pharmacy, cosmetics, the biomedical field, the food industry and biotechnologies.

In addition, since the transacylation reaction can be limited to the upper layer of the spheres, the process allows the incorporation of fragile substances including biological products, plant cells or tissues, and animal cells or tissues, or living organs or groups of tissues, or alternatively the incorporation of microorganisms, without any adverse effect.

Finally, the possibility of varying the thickness of the membrane offers the advantage of allowing an adjustment of the properties of the membrane. For example, if the spheres contain a substance active in the cosmetology field, conditions may be chosen such that the membrane is of weak mechanical strength, such that it is destroyed on application to the skin, releasing its contents. Or, on the contrary, it may be chosen for the membrane to be strong and to act as a sustained release reservoir allowing slow diffusion of the contents in situ. In this case, the variations in thickness of the membrane will also make it possible to modulate the diffusion kinetics of the contents into the external medium. In addition, the thickness of the membrane will condition its sensitivity to enzymatic lysis. Thus, in the pharmaceutical field, beads, capsules, microcapsules, spheres or microspheres may be prepared, allowing the administration of active principles by various routes, such as the oral route, the parenteral route, the rectal route or the topical route. In this way, for example, gastroresistant capsules may be prepared, the enterosolubility of which will be variable, thereby making it possible orally to administer active principles liable to be degraded by the stomach or substances that are irritant towards the gastric mucosa. These substances will be released more or less rapidly into the intestine, depending on whether the membrane is more or less rapidly degraded by the intestinal proteases. Moreover, the variations in thickness of the membranes and the choice of protein may make it possible to obtain variations in their transparency. Depending on the cases, completely transparent or transluscent or opaque membranes may be prepared. Opaque membranes may be preferred, for example, if the contents can be damaged by light.

Finally, by variations in the duration of the transacylation reaction and/or in the pH of the said reaction, the porosity of the membrane may be varied and hence this porosity may be adjusted depending on the molecular weight of the substance which it is desired to keep within the particles or alternatively to cause to diffuse out during their use. This possibility constitutes a considerable advantage of the processes according to the invention both for in vivo applications, for example those based on the release of a substance such as a hormone into the body, and for in vitro applications, in particular for the production of biological substances by cells, tissues or microorganisms which may or may not be genetically modified.

Thus, according to a first aspect, the subject of the present invention is the use of a transacylation reaction with formation of covalent amide bonds between at least one polysaccharide bearing esterified carboxylic groups and at least one polyamino substance for the manufacture, in aqueous medium, of particles, especially beads, capsules, microcapsules, spheres and microspheres, comprising, at least at the surface, a membrane formed by the reaction product according to the said transacylation reaction with formation of covalent amide bonds between the said esterified polysaccharide and the said polyamine, the said esterified polysaccharide and the said polyamine being more particularly defined in the following description in its entirety, as well as by the claims. These particles preferably contain a cosmetic or pharmaceutical active principle, or a substance of agrifood value, or a protein endowed with biological activity such as an enzyme, a hormone, an antibody or hemoglobin, or insoluble particles such as active charcoal particles, or a foam of air bubbles, or an aqueous or hydrophobic liquid phase, or a vaccine, or living animal or plant cells, tissues or organs, or eggs or seeds, or microorganisms such as bacteria or yeasts, or cell constituents such as liver microsomes, or gametes, embryos, genetic material from the animal kingdom or from the plant kingdom.

According to a second aspect, the subject of the present invention is also particles, especially beads, capsules, microcapsules, spheres or microspheres, characterized in that they comprise at least one esterified polysaccharide and at least one polyamine, having added to them at least one polysaccharide which is gellable when neither the esterified polysaccharide nor the polyamine are gellable under the operating conditions chosen, the said particle comprising, at least at the surface, a membrane formed by the product of the transacylation reaction with formation of covalent amide bonds between the esterified polysaccharide and the said polyamine, within a gel which can possibly be liquefied.

According to a production variant, the abovementioned esterified polysaccharide is a polysaccharide bearing esterified carboxylic groups, in particular a propylene glycol alginate, a pectin, in particular a high methoxyl pectin, or any other compound obtained by esterifying carboxyls of carboxyl-bearing polysaccharides.

According to another production variant, the abovementioned polyamine comprises a protein, a polypeptide, a polyamino acid, a polysaccharide bearing amino groups such as chitosan, or an aliphatic, alicyclic or aromatic organic substance bearing several primary or secondary amino groups, such as ethylenediamine, hexamethylenediamine, piperazine, phenylenediamine or polyethyleneimine.

According to another production variant, the abovementioned polysaccharide is a gellable polysaccharide, chosen in particular from the group consisting of an alginate, a carrageenan, in particular kappa-carrageenan, a gellable pectin, in particular a low methoxyl pectin, and chitosan.

Other production variants are mentioned in the description and the claims.

According to one production variant, the particles have, inside the membrane, a solid content formed of the constituent which is gellable in gelled form in particular by a mono- or polyvalent cation, such as a calcium salt, in which the encapsulated material is dissolved or dispersed.

According to another production variant, the particles are characterized in that they have, inside the membrane, a liquefied content, resulting from a subsequent liquefaction treatment of the gel within the spheres, for example by sodium citrate or sodium phosphate, which may contain substances in solution, suspension or emulsion.

According to another production variant, the particles are characterized in that they have, inside the membrane, a liquid content consisting of an aqueous or hydrophobic liquid, introduced into the particles by laminar coextrusion of the aqueous solution to be gelled and of the liquid to be encapsulated.

The proportions of gelling polysaccharide relative to the esterified polysaccharide may advantageously range from 0% to 300% by weight. The proportions of esterified polysaccharide relative to the polyamine may range from 3% to 500% by weight.

According to a particularly advantageous embodiment, these particles, in particular these beads, capsules, microcapsules, spheres or microspheres, contain an active principle chosen in particular from the group consisting of a cosmetic or pharmaceutical active principle, a substance of agrifood value, a substance of diagnostic or reagent value, a protein endowed with biological activity such as an enzyme, a hormone, an antibody or hemoglobin, or a foam of air bubbles, or insoluble particles such as particles of active charcoal, or a hydrophobic liquid phase, or a vaccine, or living cells, tissues or organs from the animal or plant kingdom, embryos, eggs, or seeds to which may be added various substances, or microorganisms such as bacteria or yeasts, or cell constituents such as liver microsomes, or gametes, embryos, genetic material from the animal kingdom or from the plant kingdom.

According to another advantageous production variant of the invention, the particles are characterized in that they have a central part consisting of an optionally gelled or liquefied aqueous phase containing a material, in particular a living material such as microorganisms, for instance yeasts or bacteria, or living cells, in particular plant cells or plant tissues, or animal cells or tissues, or a biological substance such as, for example, an enzyme, and an outer layer not containing the said material and containing, at least at the surface, a membrane formed by the product of the transacylation reaction with formation of covalent amide bonds between an esterified polysaccharide and a polyamine. Such particles may, for example, be prepared by laminar coextrusion of two aqueous phases of different composition, as will be described later in particular with reference to the seventh aspect of the invention.

This specific constitution makes it possible to lock away the material included in the central part. Any release of the said material, in particular of microorganisms or of cells, into the medium used may thus in particular be avoided. This is particularly important in fermentation processes, and especially in processes of fermentation or of refermentation for the preparation of champagne. In addition, in the case of particles, in particular beads, which are intended to be implanted for cell therapy or for enzyme therapy, the outer layer prevents any development of an immunological reaction by isolating the cells or the biological substances from the external medium.

According to a third aspect, the present invention relates to a process for the manufacture of particles, in particular beads, capsules, microcapsules, spheres or microspheres, characterized by the following successive steps:

a) a first initial aqueous solution which may be gelled by a gelling agent containing at least one esterified polysaccharide and at least one polyamine, which have added to them at least one polysaccharide which is gellable when neither the esterified polysaccharide nor the polyamine are gellable under the operating conditions chosen, is prepared, b) this first solution is dripped into a second aqueous solution forming a gelling bath, containing a gelling agent, so as to individualize particles by gelation using the said gelling agent, c) the gelled particles obtained are then placed in contact with an alkaline aqueous solution, so as to trigger the transacylation reaction, at least at the surface of the gelled particles, between the esterified polysaccharide and the polyamine which are contained in the said particles, for a predetermined period of time, in order to form a membrane at least at the surface of the said particles, d) an acidic agent is added to the reaction medium so as to neutralize and thus stabilize the particles.

As a variant, the gelling bath may be basified, or alternatively the particles are separated from the gelling bath, they are washed with water and are then dispersed in an alkaline solution, or alternatively they are dispersed in water and the suspension is then basified.

In one variant, the above procedure is applied by incorporating the polyamine both into the gellable initial aqueous phase and into the basified external phase. Compensation may thus be made for the possible losses of polyamine by diffusion outside the beads in aqueous medium.

According to a fourth aspect, the present invention relates to a process for the manufacture of particles, characterized by the following successive steps:

a) a first initial aqueous solution which is gellable by a gelling agent containing at least one esterified polysaccharide and optionally a polyamine, to which is added at least one polysaccharide which is gellable when the esterified polysaccharide is not gellable under the operating conditions chosen, is prepared, b) this first solution is dripped into a second aqueous solution forming a gelling bath containing a gelling agent, so as to individualize particles by gelation using the said gelling agent, c) the gelled particles obtained are placed in contact with an alkaline aqueous solution containing a polyamine, so as to trigger a so-called transacylation reaction, at the surface of the gelled particles, between the esterified polysaccharide contained in the said particles and the polyamine, for a predetermined period of time, in order to form a membrane at least at the surface of the said particles, d) an acidic agent is added to the reaction medium so as to neutralize and thus stabilize the particles.

The abovementioned processes may advantageously use, in order to form the drops of gellable solution, any means making it possible to individualize drops, for example such as a syringe fitted with a needle or a peristaltic pump equipped with a tube fitted with a needle or a system of dispersion by the use of a compressed-air vaporizer, or alternatively by mechanically cutting, using a vibrator, a laminar flow produced by extrusion through a nozzle.

According to a fifth aspect, the present invention provides yet another process for the manufacture of particles, in particular beads, capsules, microcapsules, spheres or microspheres, for encapsulating an aqueous or hydrophobic liquid phase, characterized in that it comprises the following successive steps:

a) a first initial aqueous solution which may be gelled by a gelling agent containing at least one esterified polysaccharide and at least one polyamine, having added to them at least one polysaccharide which is gellable when neither the esterified polysaccharide nor the polyamine are gellable under the operating conditions chosen, is prepared and an aqueous or hydrophobic liquid phase to be encapsulated is provided, b) a laminar coextrusion of the said first initial aqueous solution and of the aqueous or hydrophobic liquid phase to be encapsulated is produced through an extrusion nozzle, under conditions producing a dissociation of the laminar flow into individual droplets, for example by subjecting the laminar flow to vibrations, c) the individual droplets are dropped into a second aqueous solution containing a gelling agent so as to individualize particles by gelation using the said gelling agent, d) the gelled particles obtained are placed in contact with an alkaline aqueous solution so as to trigger the transacylation reaction, at least at the surface of the particles, between the esterified polysaccharide and the polyamine, for a predetermined period of time, in order to form a membrane at least at the surface of the said particles, e) an acidic agent is added to the reaction medium so as to neutralize and hence stabilize the particles.

According to a sixth aspect, the present invention provides yet another process for the manufacture of particles, in particular beads, capsules, microcapsules, spheres or microspheres, for the encapsulation of an aqueous or hydrophobic liquid phase, characterized in that it comprises the following successive steps:

a) a first initial aqueous solution which may be gelled by a gelling agent containing at least one esterified polysaccharide and optionally a polyamine, to which is added at least one polysaccharide which is gellable when the esterified polysaccharide is not gellable under the operating conditions chosen, is prepared, b) a laminar coextrusion of the said first initial aqueous solution and of the aqueous or hydrophobic liquid phase to be encapsulated is produced through an extrusion nozzle, under conditions producing a dissociation of the laminar flow into individual droplets, for example by subjecting the laminar flow to vibrations, c) the individual droplets are dropped into a second aqueous solution containing a gelling agent as to individualize particles by gelation, d) the gelled particles are placed in contact with an alkaline aqueous solution containing a polyamine so as to trigger the transacylation reaction, at the surface of the particles, between the esterified polysaccharide and the polyamine, for a predetermined period of time, in order to form a membrane at least at the surface of the particles, e) an acidic agent is added to the reaction medium so as to neutralize and hence stabilize the particles.

According to a seventh aspect, the present invention provides yet another process for the manufacture of particles, in particular beads, capsules, microcapsules, spheres or microspheres, containing an encapsulated material which is present exclusively in its central part, and characterized in that it comprises the following successive steps:

a) a first initial aqueous solution which may be gelled by a gelling agent containing at least one esterified polysaccharide and at least one polyamine, which have added to them at least one polysaccharide which is gellable by the said gelling agent when neither the esterified polysaccharide nor the polyamine are gellable under the operating conditions chosen, is prepared, b) an aqueous phase to be encapsulated, optionally containing at least one gellable polysaccharide and containing a material, in particular a living material such as microorganisms, for instance yeasts or bacteria, or living cells or tissues, in particular plant cells or tissues, animal cells or tissues, or groups of tissues, or a biological substance such as, for example, an enzyme, is prepared, c) a laminar coextrusion of the said first initial gellable aqueous solution as an external flow, and of the aqueous phase to be encapsulated as an internal flow, is produced through an extrusion nozzle under operating conditions producing a dissociation of laminar flow into individual droplets, for example by subjecting the laminar flow to vibrations, d) the individual droplets are dropped into a second aqueous solution containing a gelling agent so as to individualize particles by gelation, e) the particles are placed in contact with an alkaline aqueous solution to which is optionally added at least one polyamine, so as to trigger the transacylation reaction, in the outer layer of the particles, between the said esterified polysaccharide and the said polyamine, for a predetermined period of time, in order to form a membrane at least at the surface of the particles, f) an acidic agent is added to the reaction medium so as to neutralize and hence stabilize the particles.

Apparatus assemblies for carrying out this coextrusion process are well known to those skilled in the art, and these experts may refer to documents WO 92/06771 or GB-A-2,192,171 or alternatively EP-A-0,173,915 which are incorporated here in their entirety by way of reference.

The abovementioned processes may advantageously also comprise an additional step of separation of particles by any suitable means, in particular by natural settling or centrifugation, after one or more washes have been carried out.

According to an advantageous characteristic of the manufacturing process according to the invention, the particles, once separated from the reaction medium, may be placed in a solution of a liquefying agent, in particular of sodium citrate or of sodium phosphate, so as to liquefy the internal gel. Exchanges between the material encapsulated in the particles and the external medium will thus be facilitated. In addition, when this material is a living biological material, it may continue to grow and to multiply inside the particle.

According to an advantageous characteristic of the manufacturing process according to the invention, the particles may be dried, for example by freeze-drying, by spraying or in a fluidized bed dryer, for example with air advantageously heated to a suitable temperature, thereby making it possible to obtain a product which is easy to handle and to store and keeps well.

According to another advantageous characteristic of the manufacturing process, the particles may be readily produced under aseptic conditions, working in a sterile atmosphere and using sterilized starting materials, for example by radiosterilization or by sterilizing filtration.

According to another advantageous characteristic of the manufacturing process, once manufactured, the particles may be sterilized by radiosterilization. Thus, they may be used, for example, for administering active principles via the parenteral route, in human or veterinary medicine.

According to an advantageous characteristic of the manufacturing process, the polyamine is a protein, preferably chosen from hydrophilic proteins or proteins treated so as to be rendered hydrophilic, that is to say water-soluble or water-dispersible, containing free amino groups.

It is not essential for the protein materials used in the reaction to be pure proteins. They may be used in the form of natural or non-natural mixtures containing one or more hydrophilic proteins, for example such as milk or a lactoserum protein concentrate.

Examples of proteins which may be used in the invention and which satisfy the conditions, which consist in being hydrophilic or else which may be treated in order to be hydrophilic, are albumins such as serum albumin, ovalbumin, alpha-lactalbumin, globulins, fibrinogen, casein, plant proteins such as soya or wheat proteins, glutenins which have preferably been degraded, solubilized scleroproteins, collagen, atelocollagen, gelatin, gelatin hydrolysates, peptones, hemoglobin, enzymes such as catalase, alkaline phosphatase, hormones, immunoglobulins or antibodies such as monoclonal antibodies.

As examples of mixtures containing hydrophilic proteins, there may be mentioned whole milk or fully or partially skimmed milk, powdered milk, condensed milk, lactoserum proteins, whole egg, egg white, egg yolk, soya flour, soya protein concentrates, liquid soya-food preparations, coconut milk, mixtures of atelocollagen and glycosaminoglycans, blood serum, meat broth, culture media, in particular culture media for plant cells or plant tissues, for animal cells or animal tissues, or culture media for microorganisms.

According to an advantageous characteristic of the manufacturing process according to the invention, the polyamino substance is a polysaccharide bearing amino groups, for example such as chitosan.

According to an advantageous characteristic of the manufacturing process according to the invention, the esterified polysaccharide is a hydrophilic polysaccharide bearing many carboxylic groups, which are esterified in a proportion at least equal to 50%, either by chemical modification or naturally. According to a preferred characteristic, the esterified polysaccharide is chosen from propylene glycol alginate (PGA) and pectins, preferably chosen from high methoxyl pectins.

According to an advantageous characteristic of the manufacturing process according to the invention, the gellable polysaccharide is chosen from an alginate, a pectin, in particular a low methoxyl pectin, a carrageenan, in particular a kappa-carrageenan, a polysaccharide bearing amino groups which may preferably be gelled at a pH above 6.2 or in the presence of polyphosphate, such as chitosan.

According to an advantageous characteristic of the manufacturing process according to the invention, the concentration of gelling polysaccharide in the initial aqueous solution to be dispersed and gelled is between 0 and 20%, and is preferably 1% (w/v).

According to another advantageous characteristic of the process according to the invention, the concentration of esterified polysaccharide in the initial aqueous solution is between 0.5% and 20% and, further, is preferably in the region of 2% w/v.

According to another advantageous characteristic of the process according to the invention, the concentration of polyamine in the initial aqueous solution is between 1% and 30% w/v.

According to another advantageous characteristic of the process according to the invention, the concentration of monovalent or polyvalent cation, in particular of calcium salt or of potassium salt or of polyphosphate, in the gelling bath is between 0.01M and 3M, and preferably is 0.8M to 1M.

According to another advantageous characteristic of the process according to the invention, the period for which the particles are stirred in the gelling bath is between 1 and 40 minutes.

According to another advantageous characteristic of the process according to the invention, the amount of alkaline agent to add, in order to trigger the transacylation reaction, to the aqueous suspension of the gelled alginate particles or to the aqueous phase in which the spheres are directly dispersed, is such that the pH of the aqueous suspension of spheres is between 8 and 14 and, further, preferably between 10.5 and 12.5.

According to another advantageous characteristic of the process according to the invention, the amount of acidic agent to be added to the alkaline suspension of particles after the transacylation reaction is such that the water of the particle suspension is neutralized or brought to a slightly acidic pH.

According to another advantageous characteristic of the process according to the invention, the alkaline agent to add in order to trigger the transacylation reaction is, for example, chosen from sodium hydroxide, potassium hydroxide, aqueous ammonia or an amino compound such as, for example, triethanolamine, triethylamine and polyethyleneamine.

According to another advantageous characteristic of the process according to the invention, the thickness of the membrane formed by the transacylation reaction, and its resistance to enzymatic lysis, may be increased by increasing the duration of the said transacylation reaction and/or by variations in the composition of the alkaline solution which triggers the said transacylation reaction, and, in particular, by increasing the amount of alkaline agent used to prepare the said alkaline solution.

According to another advantageous characteristic of the process according to the invention, the time for which the particles are kept in the alkaline solution in order for the transacylation reaction to develop is between 5 min and 1 hour, preferably between 5 min and 30 min, and even more preferably is 15 min.

According to another advantageous characteristic of the process according to the invention, the acidic agent used to neutralize the aqueous suspension of particles after the transacylation reaction is, for example, chosen from monocarboxylic or polycarboxylic organic acids which may or may not bear alcohol functions, such as acetic acid, citric acid, tartaric acid, succinic acid, malic acid or lactic acid or an inorganic acid such as hydrochloric acid or sulfuric acid.

According to another advantageous characteristic of the process according to the invention, the neutralization time of the particles, that is to say the stirring time necessary after addition of the acid to the reaction medium, is between 5 min and 1 hour, preferably between 5 min and 30 min, and even more preferably is 15 min.

According to another advantageous characteristic of the process according to the invention, the concentration of the citrate or phosphate solution to be used in order to liquefy the contents of the particles after formation of the membrane by transacylation is between 0.01M and 1M, and is preferably in the region of 0.2 to 0.5M.

According to another advantageous characteristic of the process according to the invention, the time for which the particles, after the transacylation reaction, must be stirred in the citrate or phosphate solution in order to liquefy the contents is between 2 min and 30 min, and is preferably 10 min.

It is possible to introduce into the particles various substances which will be incorporated either into the initial gellable aqueous solution of the processes described in the third and fourth aspects, or into the aqueous or hydrophobic liquid phase to be encapsulated by coextrusion according to the processes described in the fifth, sixth and seventh aspects.

Thus, one or more active principles may be introduced into the initial aqueous phase, or into the liquid phase to be encapsulated by coextrusion, directly or in the form of a solution, a suspension or an emulsion, in particular one or more substances of cosmetic, pharmaceutical or biomedical or food value. It is possible, for example, to emulsify a hydrophobic liquid phase, such as a plant oil, a mineral oil, a silicone oil, an essential oil or an oily solution of a lipid-soluble substance, in the initial aqueous phase. The hydrophobic liquid phase may be incorporated directly by encapsulating it by coextrusion.

It is also possible to disperse particles of an adsorbent material, such as active charcoal, in the initial aqueous solution or in the liquid phase to be encapsulated by coextrusion. Such spheres containing an adsorbent material contained in a membrane have applications in particular in extracorporeal blood purifying circuits in order to free blood of its toxic metabolites (renal insufficiency) or of toxic substances in cases of poisoning. It is also possible to trap a foam inside the particles. Thus, for example, bubbles of gas such as air may be incorporated into the initial solution containing the sodium alginate, the esterified polysaccharide and the protein, by subjecting it to very vigorous stirring. The process of the invention is then applied to the foam by dripping it into the gelling bath, and then by forming a membrane around the gelled particles, by a transacylation reaction. After drying, the particles contain a multitude of trapped gas bubbles. Such particles find an indication of use in methods of medical diagnosis by echography. In addition, their low density allows them to float on the surface of water, thereby allowing other applications to be envisaged such as the preparation of forms with prolonged gastric residence in order to allow sustained release of an active principle upstream of the sites of intestinal resorption. Another advantageous application of degradable floating membraned particles is the preparation of spherules to be dispersed on the surface of water and containing a substance which is toxic to mosquito larvae. Slow release of the product at the water's surface allows a highly effective treatment with less product since it targets the larvae located at this level.

A vaccine for slow release in situ, or alternatively living material from the animal kingdom or from the plant kingdom, may also be dispersed in the initial aqueous phase or in the liquid phase to be encapsulated by coextrusion.

Examples of living material which may be incorporated into the particles according to the invention are microorganisms for carrying out syntheses or bioconversions, such as bacteria, for instance those used for fermenting dairy products, or those used for water purification, or fungi such as mycorrhizas or yeasts such as, for example, the yeasts used in the manufacture of beer, or the yeasts used to give champagne its mousse, or microalgae, seeds to which various protective substances or substances influencing their germination or their growth have optionally been added, plant somatic embryos for producing synthetic seeds, plant apices, plant cells or tissues in particular for carrying out biosyntheses or bioconversions, living material from the animal kingdom, such as cells or tissues which may be used in particular to carry out toxicology tests in vitro, such as liver cells, chondrocytes, neurones, cells or groups of cells or tissues which may be used in the context of a cell therapy, such as the islets of Langerhans for treating diabetes, medullo-adrenal cells or chromaffin cells for treating Parkinson's disease or for treating chronic pains, or cells which may be used for the production of various biological substances such as hormones, enzymes, growth factors, interferon, clotting factors, or hybridomas for production of monoclonal antibodies, or cell constituents such as liver microsomes for carrying out bioconversions, or eggs, or gametes, embryos or genetic material from the animal kingdom or from the plant kingdom.

When a protein endowed with a specific biological activity, such as an enzyme or hemoglobin, is used to react with the esterified polysaccharide, the particles obtained according to the invention may constitute an immobilized form which is easy to use, in particular in the biotechnology, bioreagent or therapeutic fields. Thus, for example, particles prepared from enzymes have indications of use in substitutive therapy in enzyme deficiencies, or in extracorporeal blood purification systems, or for catalyzing reactions in biotechnology. Particles prepared from hemoglobin have applications as artificial red blood cells or alternatively in biotechnology for the oxygenation of bioreactors.

Finally, according to an eighth aspect, the present invention further relates to a composition such as a cosmetic composition, or a pharmaceutical composition, or a food composition, or an enzyme composition, or a composition for cell therapy, or a composition for enzyme therapy, or a composition for blood purification, or a composition for diagnosis or for reagents, or a composition for toxicological tests in vitro, or a composition for coated seeds, or a composition for biotechnological production, characterized in that it comprises particles, in particular beads, capsules, microcapsules, spheres or microspheres, comprising, at least at the surface, a membrane formed by the product of reaction, according to the said transacylation reaction, with formation of covalent bonds between at least one polyamine and at least one polysaccharide bearing esterified carboxylic groups.

DESCRIPTION OF THE DRAWINGS

Other aims, characteristics and advantages of the invention will emerge more clearly on reading the explanatory description which follows, made with reference to several production examples of the invention which are given purely by way of illustration and which should thus in no way limit the scope of the invention, and with reference to the attached figures in which.

WORKING EXAMPLES

Example 1 according to the invention

Figure 1:
FIG. 1 represents a plate obtained by scanning electron microscopy of a capsule of the invention according to Example 26, showing human fibroblasts lining the inner membrane wall of the capsule.

Manufacture of spheres with solid contents and with a membrane formed from human serum albumin (HSA) and propylene glycol alginate (PGA).

a) Preparation of the initial aqueous solution 12 ml of a solution in distilled water containing 2% of a PGA having a degree of esterification between 80 and 85% (Kelcoloid S (r), KELCO International), 1% of sodium alginate (Manucol, DH, KELCO) and 5% of HSA (Centre de Transfusion Sanguine, Strasbourg) are prepared, with magnetic stirring at room temperature.

b) Individualization of the spheres by treatment with calcium chloride

Using a Gilson peristaltic pump equipped with a Tygon tube fitted with a needle, about 10 ml of this solution are added dropwise to 50 ml of 10% $CaCl_2$ solution with magnetic stirring. Stirring is continued for 10 min and the spheres formed are then rinsed several times with distilled water.

c) Formation of the membrane

The spheres are resuspended in 50 ml of distilled water with magnetic stirring.

—400 µl of 1N NaOH are added and the mixture is left stirring for 15 min.

—150 µl of 1N HCl are added and the mixture is left stirring for 15 min.

The membrane-coated spheres obtained are rinsed several times with distilled water. Solid, smooth, opalescent spheres are obtained, of diameter about 4 mm, having a clearly visible external membrane. In the form of an aqueous suspension, they may be stored for more than 3 weeks both at +4° C. and in the oven at 45° C. These spheres are intact after freeze-drying and rehydrate rapidly. They may be radiosterilized (by gamma rays, 25 kGy) without any damage.

Test of tolerance after subcutaneous implantation in animals

These tests were carried out on four anesthetized rats whose backs were shaved. Two lateral incisions were made on each animal, via which 3 to 4 freeze-dried spheres were introduced as they are, on one side, and 3 to 4 freeze-dried spheres rehydrated beforehand in sterile NaCl isotonic solution were introduced on the other side. The incisions were sutured. No appreciable inflammatory reaction was observed in the animals, and they neither displayed any edema nor developed any infection. Examination of the implantation sites after sacrificing 24 h, 3 days, one week and 2 weeks after the implantation, revealed no abnormal tissue reaction. In addition, the examination showed that the resorption of the spheres, which was well underway after one week, was very advanced after 2 weeks.

Example 2 according to the invention

Manufacture of particles with liquid contents, having a membrane formed from human serum albumin (HSA) and propylene glycol alginate (PGA).

The procedure described in Example 1 is repeated. The membrane-coated particles obtained then undergo a treatment intended to liquefy the internal gel:

Treatment with sodium citrate:

The batch of particles is resuspended in 50 ml of aqueous 10% sodium citrate solution and stirred for 10 min. The liquefied particles are then rinsed several times with distilled water.

Transparent spheres are obtained, of diameter in the region of 3.3 mm, formed of a liquid content trapped inside a thin, flexible and colorless membrane. After freeze-drying, the thin membrane is often broken.

Tests of stability of particles stored in the form of an aqueous suspension

—A batch of particles is stored in the form of a suspension in distilled water at a temperature of +4° C. No degradation of the particles is observed after storage for 6 months.

—A batch of particles is suspended in distilled water and then placed in an oven at a temperature of 45° C. No degradation was observed after 3 weeks.

Tests of in vitro degradation by proteases

Procedure: a sample of 20 particles is placed in a test tube containing:

—either a pepsin solution (from porcine stomach mucosa, SIGMA) at pH 1.2 (artificial gastric medium, USP XXI)

—or a 0.5% trypsin solution (from porcine pancreas, type II, SIGMA) in a pH 7.5 buffer.

Magnetic stirring is established in the tubes, which are placed in a water bath at 37° C. The test is repeated three times.

Results: (Average of the three tests)

The particles resist the pepsin for more than 24 h, whereas there are no longer any capsules remaining intact after incubation for 130 min in the presence of trypsin.

Example 3 according to the invention

The procedure described in Example 2 is applied using, during the step of formation of the membrane:

—800 µl of 1N NaOH for the basification

—then 300 µl of 1N HCl for the neutralization.

The vesicles obtained after liquefaction of the internal gel have a markedly thicker wall than those of Example 2 obtained using half as much sodium hydroxide. After freeze-drying, the membrane is intact and, when placed in the presence of water, rehydrates in 15 min.

Enzymatic degradation tests

—Pepsin: no degradation after 24 h.

—Trypsin: the time after which no intact particles remain is extended to 175 min.

Example 4 according to the invention

The procedure described in Example 2 is applied using, during the step of formation of the membrane:

—1,200 µl of 1N NaOH for the basification

—then 450 µl of 1N HCl for the neutralization.

The membrane of the particles obtained is very thick, thicker and less elastic than that of the capsules of Example 3. After freeze-drying, the vesicles are slower to rehydrate (90 min).

Enzymatic degradation tests

—Pepsin: no degradation after 24 h.

—Trypsin: the time after which no intact particles remain is extended to 215 min.

Example 5 according to the invention

The procedure described in Example 2 is applied using, during the step of formation of the membrane:

—1,600 µl of 1N NaOH for the basification

—then 600 µl of 1N HCl for the neutralization.

The particles virtually no longer have any liquid content, the transacylation in this case concerning deeper layers of the particles. After freeze-drying, rehydration of the spheres is obtained after 1 h.

Enzymatic degradation tests

—Pepsin: no degradation after 24 h.

—Trypsin: the time after which no intact particles remain is extended to 250 min.

The observations of the particles obtained according to the procedures of Examples 2, 3, 4 and 5 clearly show that the thickness of the membrane may be modified and its sensitivity to protease lysis may be varied by varying the volumes of sodium hydroxide added to trigger the transacylation reaction.

Example 6 according to the invention

Manufacture of spheres with a membrane formed from HSA and PGA, and containing particles of active charcoal.

The procedure described in Example 3 is applied by dispersing, into the initial aqueous phase, 600 mg of particles of active charcoal (particle size of 125 to 315 µm) and by using a syringe in order to add this suspension to the calcium solution. Black spheres are obtained, of size in the region of 4 mm, in which the particles of charcoal may be distinguished. These particles are intact after freeze-drying.

Example 7 according to the invention

Aseptic manufacture of particles with a membrane formed from HSA and PGA.

The procedure described in Example 3 is repeated, using starting materials (sodium alginate, HSA and PGA) which are sterilized by gamma rays (25 kGy) and sterile water for injectable preparations. The manufacture is performed under laminar flow. Uniform spheres surrounded by a membrane which appears perfectly formed after the liquefaction treatment with sodium citrate are obtained.

Example 8 according to the invention

Manufacture of particles with a membrane formed from HSA and PGA and containing air bubbles.

The procedure described in Example 3 is applied, adding a step of incorporation of air bubbles into the initial aqueous phase and using a syringe to add the foam thus obtained to the calcium solution.

To this end, the initial solution containing the sodium alginate, the PGA and the HSA is subjected to mechanical stirring at 2000 rpm for 5 min, thereby producing a foam. The foam is then added dropwise to the calcium solution with magnetic stirring, and the following operations are carried out as described in Example 3. Next, after formation of the membrane by basification and then neutralization by acidification of the particle suspension, the membrane-coated particles are rinsed several times with distilled water and resuspended in distilled water. The suspension is then divided into two parts. After separation by centrifugation, half of the batch is resuspended in 25 ml of 10% sodium citrate solution and stirred for 10 min. The liquefied spheres are then rinsed several times with distilled water. The other part of the batch is kept in aqueous suspension.

The non-citrated particles float on water, are spherical, white, opaque and hard and air bubbles may be seen at the edge. They are intact after freeze-drying, rehydrate slowly and float on water. After liquefaction with citrate and reswelling in water, the diameter of the particles increases and the membrane formed of a stiffened foam is clearly seen.

Example 9 according to the invention

Manufacture of particles with a membrane formed from ovalbumin and PGA.

The procedure described in Example 1 is applied, by replacing the HSA by ovalbumin (OSI), by increasing the protein concentration to 8% and by doubling all the amounts of reagents.

After formation of the membrane and neutralization with HCl of the particle suspension, the latter is divided into two parts:
—one undergoes the liquefaction treatment with sodium citrate, as described in Example 2,
—the other does not undergo a liquefaction treatment.

The particles not treated with citrate are egg-shaped and opalescent in appearance. In aqueous suspension form, they may be stored for more than 3 weeks both at +4° C. and in the oven at 45° C. They are intact after freeze-drying and rehydrate rapidly. The particles treated with citrate are perfectly spherical and transluscent. In aqueous suspension form, they may be stored for more than 3 weeks both at +4° C. and in the oven at 45° C. Many are broken after the freeze-drying treatment.

Example 10 according to the invention

The procedure described in Example 9 is repeated using twice the volume of sodium hydroxide solution and of acidic solution.

Whereas, before the basification treatment, the gelled alginate particles have the form of transluscent, beige, egg-shaped beads, after basification of the suspension and then neutralization, they become much more opaque and harder in consistency. After the liquefaction treatment with citrate, the particles become soft and transluscent. They have a thick wall, and gradually resume a spherical shape after remaining for some time in distilled water. They are fully resistant to the freeze-drying treatment and rehydrate in 5 to 10 min.

Example 11 according to the invention

The procedure described in Example 9 is repeated using three times the volume of sodium hydroxide solution and of acidic solution.

Before liquefaction with citrate, the particles, which are opaque, have a thicker wall and are harder in consistency than the particles of Example 10. After liquefaction with citrate, they become more transluscent and softer. They are fully resistant to freeze-drying and rehydrate in about 1 h 30.

Example 12 according to the invention

Manufacture of particles with a membrane formed from ovalbumin and PGA and containing olive oil.

The procedure described in Example 9 is repeated, by emulsifying 4.8 ml of olive oil in the initial aqueous solution by mechanical stirring at 5,000 rpm for 5 min. After formation of the membrane and acidification of the suspension, white beads which float on water are obtained. Oil droplets are visible in the spheres, under a microscope. After liquefaction of the internal gel with citrate, the beads are softer and flatter. They become spherical again after remaining in distilled water for a few hours. The center of the particles is in the form of a fluid emulsion.

Example 13 according to the invention

Manufacture of particles with a membrane formed from ovalbumin and PGA and containing essential oil of peppermint.

The procedure described in Example 12 is repeated, replacing the olive oil by essential oil of peppermint.

The appearance of the particles obtained before and after treatment with citrate is comparable with that of the particles prepared according to Example 12.

Example 14 according to the invention

Manufacture of particles with a membrane formed from ovalbumin and pectin.

The procedure described in Example 10 is repeated, replacing the PGA by apple pectin (FLUKA, 70 to 75% esterification).

The particles treated with sodium citrate, like the untreated particles, are similar to the particles prepared from PGA according to Example 10. After freeze-drying, the spheres are intact and have a clearly visible membrane. They are rapidly rehydrated (10 min).

Example 15 according to the invention

Manufacture of particles with a membrane formed from bovine serum albumin (BSA) and PGA.

The procedure described in Example 10 is repeated, replacing the ovalbumin by bovine serum albumin (fraction V, SIGMA) used at a concentration of 2%. The particles have characteristics comparable to those of the particles prepared according to Example 10. After treatment with citrate, the particles may be stored in the form of an aqueous suspension for more than 3 weeks, both at +4° C. and in the oven at 45° C.

Example 16 according to the invention

Manufacture of particles with a membrane formed from hemoglobin and PGA.

The procedure described in Example 10 is repeated, replacing the ovalbumin by bovine hemoglobin (SIGMA) used at a concentration of 10%. The particles have characteristics comparable to those of the particles prepared according to Example 10. After treatment with citrate, the particles may be stored in the form of an aqueous suspension for more than 3 weeks, both at +4° C. and in the oven at 45° C.

Example 17 according to the invention

Manufacture of particles with a membrane formed from lactoserum proteins and PGA.

The procedure described in Example 10 is reproduced, replacing the ovalbumin by a lactoserum protein concentrate (Prosobel S65E, Bel Industries) used at a concentration of 5%.

The particles have characteristics comparable to those of the particles prepared according to Example 10. After treatment with citrate, the particles may be stored in the form of an aqueous suspension for more than 3 weeks, both at +4° C. and in the oven at 45° C.

Example 18 according to the invention

Manufacture of particles with a membrane formed from a gelatin hydrolysate and PGA.

The procedure described in Example 10 is repeated, replacing the ovalbumin by a gelatin hydrolysate which is soluble in cold water (DSF atomized gelatin, Méro-Rousselot-Satia) used at a concentration of 10%.

The particles have characteristics comparable to those of the particles prepared according to Example 10. After treatment with citrate, the particles may be stored in the form of an aqueous suspension for more than 3 weeks, both at +4° C. and in the oven at 45° C.

Example 19 according to the invention

Manufacture of particles with a membrane formed from soya proteins and PGA.

The procedure described in Example 10 is repeated, replacing the ovalbumin by soya flour (type I: not roasted, SIGMA). In order to prepare the aqueous phase, the following process is thus performed: 10% of soya flour is added to 20 ml of distilled water. After magnetic stirring for 15 min, the medium is centrifuged for 3 min at 5,000 rpm. 1% of sodium alginate and 2% of PGA are dissolved in 12 ml of the supernatant.

The particles have characteristics comparable to those of the particles prepared according to Example 10. After treatment with citrate, the particles may be stored in the form of an aqueous suspension for more than 3 weeks, both at +4° C. and in the oven at 45° C.

Example 20 according to the invention

Manufacture of particles with a membrane formed from ovalbumin and PGA and containing phenol red.

The procedure described in Example 9 is repeated, by halving the amounts of reagents, by dissolving 6 mg of phenol red in the initial solution containing the alginate, the PGA and the ovalbumin and by eliminating the liquefaction stage. The initial solution is golden yellow.

After addition of the sodium hydroxide solution which triggers the transacylation reaction, the particles are observed under a microscope. In the 15 min following the addition, there is no change in the yellow color of the core of the particles. On the other hand, the upper layer is colored fuchsia pink, thereby indicating the basification of the edge of the gel. This observation is confirmed by examination of the particles after incision of the peripheral part.

This experiment with a pH indicator dye shows that, under the test conditions, the transacylation reaction is localized in the upper layer of the spheres, since the pH variations do not reach the center thereof. The quite localized reaction may thus be applied to the encapsulation of cells and other living materials.

Example 21 according to the invention

Manufacture of particles with a membrane formed from ovalbumin and PGA and containing lactobacilli.

The experiment was carried out using freeze-dried lactobacilli, Lactobacillus casei var. rhamnosus, provided as 250 mg gelatin capsules containing at least $8 \times 10^8$ microorganisms/gram (Antibiophilus(r), Lyocentre).

* Encapsulation of the bacteria

The following are dissolved in 12 ml of sterile distilled water:
— 240 mg of PGA
— 120 mg of sodium alginate
— 720 mg of ovalbumin 240 mg of freeze-dried bacterial powder are dispersed in this solution and the spheres are prepared as described in Example 1. After formation of the membrane by transacylation and neutralization, and rinsing with sterile distilled water, the bacterial spheres are immediately used for the milk fermentation tests.

* Milk fermentation tests

Nactalia semi-skimmed milk in sterile 200 ml cartons is used.

Experimental procedure (in duplicate)

The pH of various samples of 50 ml of milk is measured at time zero, after 24 h and after 30 h of gentle magnetic stirring at the temperature of the laboratory:
— samples of pure milk (without addition of microspheres or of bacteria)
— samples of milk supplemented with a batch of microspheres containing 240 mg of lactobacilli
— samples of milk supplemented with 240 mg of free lactobacilli
— samples of milk supplemented with a batch of bacteria-free microspheres.

Results

Table 1 collates the average results obtained. The initial pH of the milk was 6.75. It is seen that it changes spontaneously to lower to 6 after 30 h (control samples: only milk).

When bacteria-free spheres are added to the milk, the pH lowers slightly less than in the control samples.

On the other hand, it is observed that the encapsulated bacteria have a pronounced activity on the pH of the milk, which is lower after 30 h than in the case of samples supplemented with free bacteria.

It is possible that the sphere contents, which liquefy during the experiment, exert a favorable effect by constituting a food for the bacteria.

Example 22 according to the invention

Manufacture of particles with a membrane formed from ovalbumin and PGA and containing Artemia salina eggs.

This experiment was carried out using dry eggs from Artemia salina, which are marketed as fish food for aquariums (Hobby).

* Encapsulation

The polymer solution is prepared as described in Example 20, but by dissolving the NaCl at a concentration of 3% in the 12 ml of water, before dissolving the polymers therein.

240 mg of dry eggs from Artemia salina are dispersed in the solution thus obtained and the procedure described in Example 2 is applied to this suspension. The capsules obtained are next rinsed with water, and then with water supplemented with 3% NaCl. They are finally dispersed in water supplemented with 3% NaCl and left at the temperature of the laboratory.

* Results

The particles are examined under a microscope at regular time intervals. Less than 24 h after the encapsulation, the eggs hatch inside the microcapsules and the movements of the crustaceans are very visible through the transparent membrane. The encapsulation process is thus fully compatible with maintenance of the viability of living organisms.

Example 23 according to the invention

Manufacture of particles with a membrane formed from alkaline phosphatase and PGA.

The procedure described in Example 3 is repeated, replacing the human serum albumin by alkaline phosphatase (type I-S, SIGMA).

After liquefaction of the gel, the liquefied spheres are rinsed several times with distilled water. They are then frozen and freeze-dried.

* Assay of the enzyme activity of the alkaline phosphatase spheres

— Principle:

The assay consists in carrying out a spectrophotometric determination (reading at 405 nm) of the amount of para-nitrophenol (pNP) released by hydrolysis of para-nitrophenyl phosphate (pNPP) at 37° C.

—Preparation of the reagents

The following reagents are prepared:

—100 mM glycine buffer, pH 10.4, containing 1 mM $MgCl_2$ and 1 mM $ZnCl_2$.

—1 mM $MgCl_2$ solution

—60 mM para-nitrophenyl phosphate solution

—0.2M NaOH solution

\* Assay procedure

A determination of the activity of the free alkaline phosphatase (non-encapsulated: FAP) and of the activity of the alkaline phosphatase immobilized in the form of freeze-dried spheres is carried out in parallel.

The conditions are featured in Table 2.

The amounts of pNP released in the two series of tests are evaluated after 1 min, 2 min and 3 min. All the tests are duplicated.

\* Results

Figure 3:
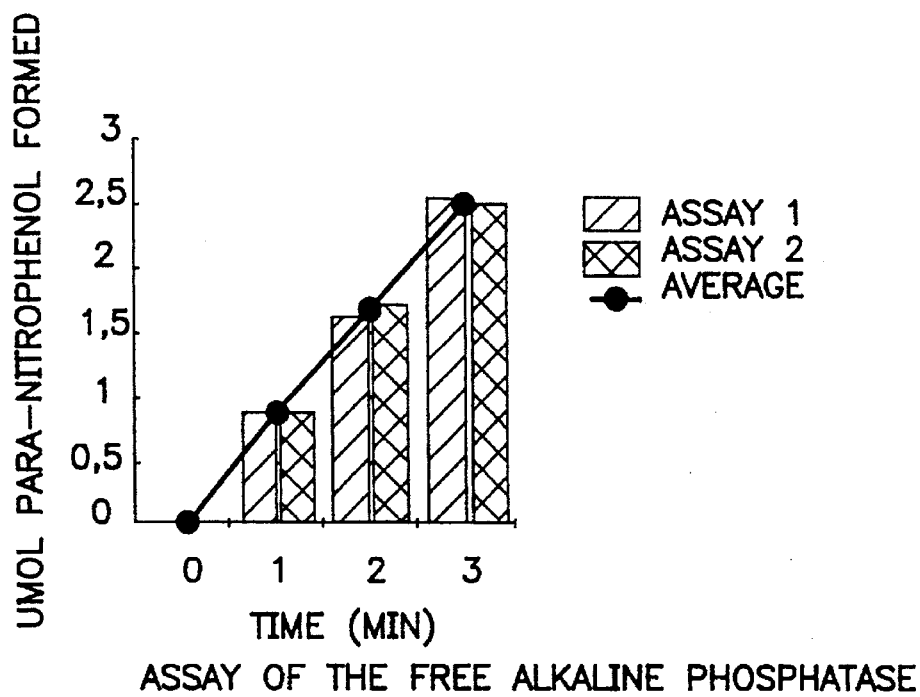
FIG. 3 shows, in µmol of para-nitrophenol released as a function of time (in minutes), the results of the enzyme activity assay of free alkaline phosphatase, used an control in Example 23 according to the invention.
Figure 4:
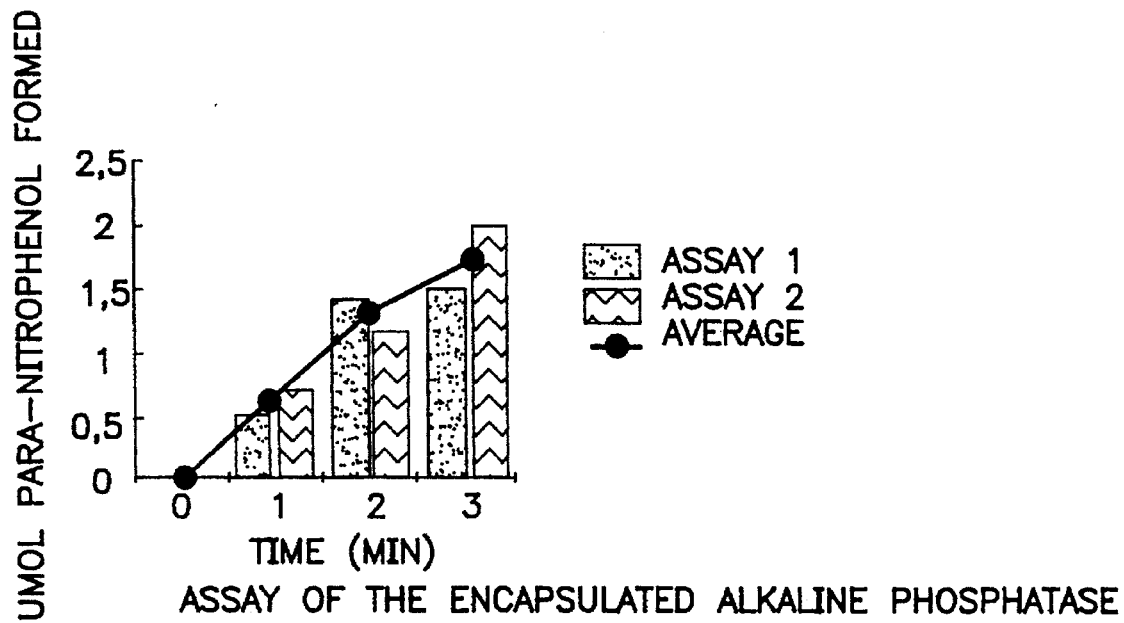
FIG. 4 shows, in µmol of para-nitrophenol released as a function of time (in minutes), the results of the enzyme activity assay of the beads of alkaline phosphatase of the invention which are prepared according to Example 23.

They are grouped together in Table 3 and FIGS. 3 and 4.

The results are expressed as units per mg of pure enzyme or of spheres, the unit being defined as the amount capable of hydrolyzing one μmol of substrate per minute under the defined experimental conditions.

It is thus observed that the spheres, with an average activity of 0.6227 units per mg, have an enzyme activity equal to 11.1% of that of the pure enzyme. Given that 1 mg of spheres contains a maximum of 0.625 mg of alkaline phosphatase, the enzyme encapsulated has retained at least 17.7% of its activity.

Example 24 according to the invention Manufacture of particles with a membrane formed from PGA added to the initial solution, and from ovalbumin added to the external phase.

a) Preparation of the initial solution

The following are dissolved in 12 ml of distilled water:

—sodium alginate at a concentration of 1%

—PGA at a concentration of 2%.

b) Individualization of the spheres by treatment with calcium chloride

The process is performed as described in Example 1.

c) Formation of the membrane

The spheres are suspended in 50 ml of aqueous 5% ovalbumin solution, for 5 min with magnetic stirring. Then —1.6 ml of 1M NaOH are added and the mixture is left stirring for 15 min.

—1.2 ml of 1M HCl are added and the mixture is left stirring for 15 min.

The membrane-coated spheres obtained are rinsed several times with distilled water.

d) Liquefaction of the gel

The sodium citrate treatment described in Example 2 is applied to the spheres.

After treatment with citrate, the spheres lose their opalescent appearance and become transparent. They then take the form of non-spherical vesicles which have a perfectly visible membrane. After suspension for 5 min in water, the spheres resume a spherical shape by swelling in the water. Their diameter becomes about twice that of the alginate-PGA spheres obtained in the calcium solution. These transparent spheres become blue on contact with dilute methylene blue solution.

Example 25 according to the invention

Manufacture of particles with a membrane formed from ovalbumin and PGA and containing watercress seeds.

The procedure described in Example 10 is repeated, dispersing 480 mg of watercress seeds (Vilmorin) in the initial aqueous phase.

After individualization in the calcium solution, the spheres, which are white, contain a variable number of seeds.

After the liquefaction treatment with titrate, the spheres are softened but do not allow the seeds to escape. After rinsing with water and suspending in water, the spheres reswell instantly.

Germination: The following are respectively placed in three Petri dishes provided with hydrophilic cotton wool soaked in water, at room temperature (20° C.):

—about ten spheres filled with seeds and not treated with citrate,

—about ten spheres filled with seeds and treated with citrate,

—and non-encapsulated seeds.

After 24 h, whereas the non-encapsulated seeds are not modified, in the spheres, either treated or not treated with citrate, shoots may be seen emerging from the seeds, these being seen by transparency through the membranes. After 3 days, the naked seeds have begun to germinate whereas the shoots of the encapsulated seeds have pierced the membrane and are already well developed.

Example 26 according to the invention

Manufacture of particles with a membrane formed from ovalbumin and PGA and containing human skin fibroblasts.

All of the operations described below are performed under sterile conditions: manipulations under a laminar flow hood, use of presterilized equipment.

a) preparation of the initial aqueous phase

The following are dissolved in 12 ml of PBS ("phosphate buffered saline", calcium-free and magnesium-free, Gibco):

—240 mg of PGA

—120 mg of sodium alginate (Laserson and Sabetay)

—720 mg of egg white albumin (Laserson and Sabetay).

The solution is centrifuged at low speed for a few minutes, so as to remove the air bubbles.

b) Incorporation of the fibroblasts

Human skin fibroblasts, pre-cultured as monolayers in culture dishes, are harvested by treatment with trypsin and then suspended in fetal calf serum and dispersed in the above solution at an amount of 50,000 cells/ml.

c) Formation of the spheres

This suspension is poured dropwise, using a syringe and a needle, into 50 ml of aqueous 10% $CaCl_2$ solution, with magnetic stirring. The stirring is continued for 5 min. The spheres are then rinsed several times with distilled water.

d) Formation of the membrane

The spheres are resuspended in 50 ml of distilled water with magnetic stirring. 50 μl of 1M NaOH are added to the suspension and the reaction is allowed to develop for 5 min. 50 μl of 1M HCl are then added to the suspension and the stirring is continued for 5 min. The spheres are then rinsed several times with distilled water and then with PBS. After incision of the membrane, the encapsulated cells are clearly seen, these appearing as small refringent spheres.

e) Culturing

The spheres containing the cells are incubated in a culture medium (DMEM, Gibco) containing 10% fetal calf serum and 2 mM glutamine. The mixture is introduced into an incubator, in an atmosphere containing 5% $CO_2$, at 37° C. The culture medium is changed regularly. Periodic examination of the spheres at each change of medium shows a gradual increase in the number of cells encapsulated. The fibroblasts thus proliferate uniformly within the spheres, as shown in the plate of FIG. 1, obtained by scanning electron microscopy.

Example 27 according to the invention

Manufacture of particles 20–100 μm in diameter, with a membrane formed from ovalbumin and PGA.

a) Preparation of the initial aqueous solution

The following are dissolved in 50 ml of distilled water:
—500 mg of PGA
—500 mg of sodium alginate
—2.5 g of ovalbumin.

The mixture is stirred until dissolution is complete and the air bubbles are then allowed to leave spontaneously over 15 min.

b) Formation of the microspheres

This solution is sprayed as fine droplets, using a compressed-air vaporizer, into 500 ml of aqueous 10% $CaCl_2$ solution, with stirring. The stirring is continued for 10 min.

c) Formation of the membrane 8 ml of 1M NaOH are added and the mixture is stirred for 15 min.

8 ml of 1M HCl are added and the mixture is stirred for 15 min.

The membrane-coated microspheres are then centrifuged and rinsed several times with distilled water.

d) Liquefaction of the gel

Half of the sediment is resuspended in 50 ml of aqueous 10% sodium citrate solution for 10 min, and the liquefied microspheres are then rinsed several times with distilled water and kept in aqueous suspension. Membrane-coated microspheres which have a diameter between 20 and 100 μm are obtained.

Example 28 according to the invention

Manufacture of particles with a membrane formed from ovalbumin and PGA.

The procedure described in Example 10 is applied, eliminating the sodium alginate from the initial aqueous phase and using the PGA at a concentration of 5% and the ovalbumin also at a concentration of 5%. The gelation step is continued for 30 min while increasing the concentration of the calcium chloride solution to 30%. Stable spheres with a clearly visible membrane are obtained.

Example 29 according to the invention

Manufacture of particles with a membrane formed from ovalbumin and containing borage oil.

a) Preparation of the initial aqueous solution

The following are dissolved in 600 ml of distilled water:
—12 g of PGA (Kelcoloid S, Kelco)
—6 g of sodium alginate (Manncol DH, Kelco)
—36 g of ovalbumin (Laserson and Sabetay)

The mixture is stirred until dissolution is complete, and the air bubbles are then allowed to leave.

b) Formation of the spheres by coextrusion and gelation

Figure 2:
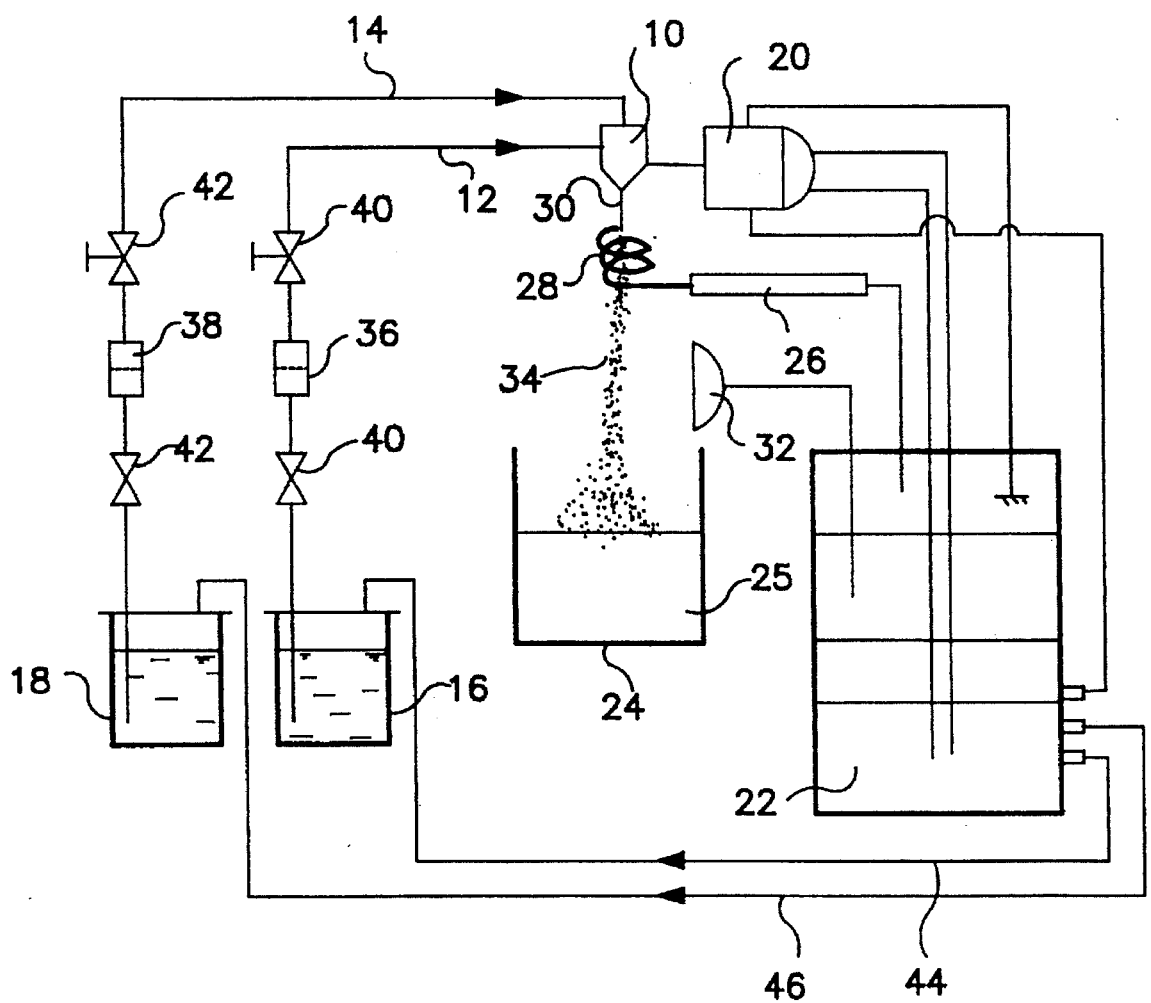
FIG. 2 represents an apparatus for manufacturing particles according to the invention, in particular in the form of beads, capsules, microcapsules, spheres or microspheres, by laminar coextrusion, with reference to Example 29.

To do this, the Extramet machine represented schematically in the attached FIG. 2 is used. This machine essentially comprises an extrusion nozzle 10 which makes it possible to perform a coextrusion by the presence of two concentric apertures supplied separately by two supply pipes 12 and 14 which serve respectively for the external supply with ovalbumin-PGA-sodium alginate solution according to the invention from a reservoir 16, and for the internal supply with borage oil from a reservoir 18. With this nozzle 10 is associated a vibrator device 20 controlled by control means 22. This device also comprises a nonadjacent gelling bath 24 under the nozzle 10, in which is placed the solution 25 of 10% $CaCl_2$. This machine also comprises an electrode 26 with a helical end arranged concentrically to the direction of flow of the laminar flow 30 coextruded from the nozzle 10, so as to keep the droplets generated by the vibrator 20 separate. A flash stroboscope device 32 may also be provided in order to observe visually the droplets thus generated falling into the gelling bath. The flow rate of the ovalbumin-PGA-sodium alginate solution in the reservoir 16 is 1 l/h and that of the borage oil in the reservoir 18 is 250 ml/h. The frequency of vibration of the vibrator 20 is 230 Hz. The diameters of the two concentric apertures are 350 and 400 μm.

The droplets 34 generated by the vibrator 20 from the laminar flow produced in the coextrusion nozzle 10 are received in 11 of gelling solution 25 kept under magnetic stirring. The bath is renewed after extrusion of 250 g of the ovalbumin-PGA-sodium alginate solution. The spheres formed are washed several times with distilled water.

c) Formation of the membrane

The spheres are suspended in 2.5 l of distilled water with magnetic stirring.
—20 ml of 1N NaOH are added and the mixture is left stirring for 15 min.
—7.5 ml of 1N HCl are added and the mixture is left stirring for 15 min.

The spheres obtained are rinsed several times with distilled water. Smooth spheres 1.5 mm in diameter and containing a droplet of borage oil are obtained.

Example 30 according to the invention

Manufacture of particles with a membrane formed from ovalbumin a) Preparation of the initial aqueous solution The following are dissolved in 600 ml of distilled water:
—12 g of PGA (Kelcoloid S, Kelco)
—6 g of sodium alginate (Manucol DH, Kelco)
—36 g of ovalbumin (Laserson and Sabetay)

The mixture is stirred until dissolution is complete, and the air bubbles are then allowed to leave.

b) Formation of the spheres by extrusion and gelation

The extrusion and the gelation of the spheres are performed under the same conditions as those described in Example 29, except for as regards the extrusion nozzle 10, which contains only a single 250 μm aperture.

c) Formation of the membrane

The procedure for formation of the membrane described in Example 29 is applied. Smooth opalescent spheres 1.4 mm in diameter are obtained.

Example 31 according to the invention

Manufacture of particles with a membrane formed from chitosan.

A solution of chitosan (Seacure 143, Pronova Biopolymer) at a concentration of 5% in 1M acetic acid is prepared. The solution is adjusted to pH 5.6 using 5M sodium hydroxide, and 2% PGA is then added. 12 ml of this solution are added dropwise to 50 ml of 1M sodium hydroxide with magnetic stirring. The stirring is continued for 10 min. The suspension is then neutralized using 1M HCl. The beads obtained are rinsed several times with water. The beads are white and opaque. The presence of a membrane is demonstrated after soaking the beads in an HCl solution of pH 2: after 5 min, the chitosan trapped inside the membrane has dissolved and transparent vesicles with a membrane formed of PGA associated with the chitosan are obtained.

Example 32 according to the invention

Manufacture of particles with a membrane formed from polyethyleneimine.

A solution containing 2% PGA and 1% sodium alginate in distilled water is prepared. 12 ml of this solution are added dropwise to 50 ml of 1M sodium hydroxide. After magnetic stirring for 10 min, the beads obtained are rinsed with water. The beads are resuspended in an alkaline bath consisting of 50 ml of water to which are added 500 mg of a commercial (SIGMA) solution of polyethyleneimine at a concentration of 50% (w/v) in distilled water. Magnetic stirring is established. After 20 min, the suspension is neutralized using 1M HCl. Transluscent beads with a thin membrane are obtained. After liquefaction using citrate, completely transparent vesicles of increased diameter are obtained.

TABLE 1

Encapsulated lactobacilli: Effect on the pH of the milk

|  | pH after 24 h | pH after 30 h |
| --- | --- | --- |
| Only milk | 6.28 | 6.00 |
| Milk + capsules containing 240 mg of bacteria | 6.06 | 5.41 |
| Milk + 240 mg of free bacteria | 6.02 | 5.78 |
| Milk + empty capsules | 6.29 | 6.35 |

The variations in pH of the milk (50 ml, initial pH=6.75) are the average of two tests performed at room temperature and with magnetic stirring.

TABLE 2

Procedure for assay of the enzyme activity of the alkaline phosphatase spheres

|  | Assay FAP* | Blank FAP | Assay BEADS | Blank BEADS |
| --- | --- | --- | --- | --- |
| Glycine buffer pH 10.4 | 2.6 ml | 2.6 ml | 13 ml | 13 ml |
| FAP in 1 mM MgCl$_2$ | 100 µg | — | — | — |
| FAP beads | — | — | 15 mg | — |
| 1 mM MgCl$_2$ | — | 100 µl | 500 µl | 500 µl |
|  | Temperature set for 15 min on a water bath at 37° C. | | | |
| 60 mM pNPP solution | 300 µl | 300 µl | 1.5 ml | 1.5 ml |
| Number of µmol of pNPP | 18 µmol | 18 µmol | 90 µmol | 90 µmol |
| Final pNPP concentration | 6 mM | 6 mM | 6 mM | 6 mM |
| Quench: 0.2 N NaOH | 3 ml after 1 or 2 or 3 min | | 15 ml after 1 or 2 or 3 min | |
| Dilution | to 1/20 or to 1/40 with 0.2 N NAOH in 20 ml volumetric flasks | | | |
| Assay | O.D. reading on a spectrophotometer at 405 nm against the blank | | | |

*FAP = free alkaline phosphatase (non-encapsulated)

TABLE 3

Results of the assay of the enzyme activity of the alkaline phosphatase spheres and comparison with the free enzyme
Table 3-A
Assay of the free alkaline phosphatase (FAP)

| µmol pNP / min | Assay 1 | Assay 2 |
| --- | --- | --- |
| 1 min | 0.8627 | 0.8432 |
| 2 min | 0.8238 | 0.84 |
| 3 min | 0.8519 | 0.8324 |
| Average per test | 0.8461 | 0.8385 |
| Units per mg of FAP | 5.64 | 5.59 |
| General average | 5.615 U/mg FAP | |

Table 3-B
Assay of the alkaline phosphatase spheres

| µmol pNP / min | Assay 1 | Assay 2 |
| --- | --- | --- |
| 1 min | 0.5505 | 0.7204 |
| 2 min | 0.7108 | 0.5766 |
| 3 min | 0.5112 | 0.6668 |
| Average per test | 0.5908 | 0.6546 |
| General average | 0.6227 U/mg | |

We claim:

1. A particle comprising at least one esterified polysaccharide and at least one polyamine, and further a gellable polysaccharide when neither the esterified polysaccharide nor the polyamine arc gellable under the conditions used for preparing said particle, said particle comprising, at least an outer membrane formed by a transacylation reaction with formation of covalent amide bonds between the esterified polysaccharide and the polyamine.

2. The particle of claim 11, in the form of of a bead, capsule, a microcapsule, a sphere or a microsphere.

3. The particle of claim 1, wherein said membrane is within a gel obtained by gelling a gellable entity selected from the group consisting of said polyamine when it is gellable, said esterified polysaccharide when it is gellable, and said gellable polysaccharide.

4. The particle of claim 1, wherein said esterified polysaccharide is a hydrophilic polysaccharide having carboxylic groups which are esterified to a proportion at least equal to 50%.

5. The particle of claim 1, wherein said esterified polysaccharide is selected from the group consisting of an esterified alginate, a pectin, and a polysaccharide having carboxyl groups which are at least partially esterified.

6. The particle of claim 5, wherein said esterified alginate is a propylene glycol alginate, and said pectin is a high methoxylated pectin.

7. The particle of claim 1, wherein said polyamine is selected from the group consisting of a protein, a polypeptide, a polyamino acid, a polysaccharide having amino groups, an aliphatic organic substance having several primary or secondary amino groups, an alicyclic organic substance having several primary or secondary, amino groups and an aromatic organic substance having several primary or secondary amino groups.

8. The particle of claim 1, wherein said polysaccharide having amino groups is a chitosan, said aliphatic organic substance having several primary or secondary amino groups is selected from the group consisting of ethylenediamine, pentamethylenediamine and hexamethylenediamine, and said aromatic organic substance having several primary or secondary amino groups is selected from the group consisting of piperazine, phenylenediamine and polyethyleneimine.

9. The particle of claim 1, wherein said at least one polyamineisa protein selected from the group consisting of a hydrophilic protein, a non-hydrophilic protein containing free amino groups treated to be water-soluble or water-dispersible, containing free amino groups.

10. The particle of claim 1, wherein said at least one polyamine is a protein selected from the group consisting of albumins, globulins, fibrinogen, casein, solubilized scleroproteins, collagen, atelocollagen, gelatin, gelatin hydrolysates, peptones, hemoglobin, plant proteins, glutenins, enzymes, hormones, immunoglobulins, antibodies, polypeptides, polyamino acids, a natural mixture containing one or more of said proteins, a non-natural mixture containing one or more of said proteins, a mixture of atelocollagen and glycosaminoglycans, whole milk, skimmed mild, partially skimmed milk, condensed milk, powdered milk, lactoserum proteins, whole egg, egg white, egg yolk, soya flour, soya protein concentrates, liquid soyafood preparations, coconut milk, blood serum, meat broth, culture media, animal cells, animal tissues and a media for culturing microorganisms.

11. The particle of claim 11, wherein said polysaccharide is a gellable polysaccharide selected from the group consisting of an alginate, a carrageenan, a gellable pectin, and a polysaccharide bearing amino groups gellable at a pH above about 6.2 or in the presence of a polyphosphate.

12. The particle of claim 11, wherein said carrageenan is kappa-carrageenan, said gellable pectin is a low methoxylated pectin and said polysaccharide having amino groups is chitosan.

13. The particle of claim 11, further containing a liquid content selected from the group consisting of a liquefied gel and an encapsulated liquid said liquid content being trapped by said membrane.

14. The particle of claim 11, wherein said membrane surrounds a gelled core obtained by gelling a gellable entity selected from the group consisting of said gellable polysaccharide, said esterified polysaccharide and said polyamine.

15. The particle of claim 11, consisting of a gel stiffened throughout its mass by a transacylation reaction product between the esterified polysaccharide and the polyamine.

16. The particle of claim 11, wherein the relative weight proportion of esterified polysaccharide to the polyamine ranges between 3% and 500%.

17. The particle of claim 11, wherein the relative proportion by weight of gellable polysaccharide to the esterified polysaccharide ranges between 0% and 300%.

18. The particle of claim 11, further containing at least one active substance selected from the group consisting of a cosmetically active substance, a pharmaceutically active substance, a substance of agrifood value, a diagnostic substance, a reagent substance, a protein having biological activity, an insoluble particle, a hydrophobic liquid phase, a solution of one or more substances in a hydrophobic liquid phase, a foam containing bubbles of gas, vaccine for slow release in situ, a living material, cells, an animal tissue, a plant tissue, a plant organ, an animal organ, a cell constituent, an animal genetic material and a plant genetic material.

19. The particle of claim 18, wherein said protein having biological activity is selected from the group consisting of an enzyme, a hormone, an antibody and hemoglobin, said insoluble particle is a particle of an adsorbent material, said hydrophobic liquid phase is selected from the group consisting of a plant oil, a mineral oil, a silicone oil and an essential oil, said gas is air.

20. The particle of claim 19, wherein said living material is selected from the group consisting of a microorganism, a fungi, a microalgae, seeds, plant somatic embryos for producing synthetic seeds, plant apices, plant cells, plant tissues, animal cells, animal tissues, and genetically modified cells.

21. The particle of claim 19, wherein said living material is selected from the group consisting of a bacteria for fermentation of dairy products, a bacteria for water purification, a mycorrhiza, yeasts, yeasts for beer manufacture, yeasts for champagne manufacture, liver cells, chondrocytes, neurones, cells for therapy, islets of Langerhans for the treatment of diabetes, medullo-adrenal cells, chromaffin cells for the treatment of Parkinson's disease, chromaffin cells for the treatment of chronic pains, growth factors, interferon, coagulation factors, hybridomas for the production of monoclonal antibodies, gametes, and embryos.

22. The particle of claim 1, which has a central part consisting of an aqueous phase under a form selected from the group consisting of a gelled form and a liquefied form, containing a material, and an external layer not containing said material and comprising, at least at the surface, said membrane.

23. The particle of claim 22, wherein said material is selected from the group consisting of a microorganism, yeasts, bacteria, living cells, plant cells, plant tissues, animal cells, animal tissues, groups of cells, groups of tissues, and a biological substance.

24. A process for the manufacture of particles comprising the following successive steps:

a) preparing a first initial gellable aqueous solution containing at least one esterified polysaccharide and at least one polyamine, and further at least one gellable polysaccharide when neither the esterified polysaccharide nor the polyamine are gellable under the conditions used for gelation in step (b), b) dripping said first solution into a second aqueous solution forming a gelling bath containing a gelling agent thereby individualizing particles by gelation caused by said gelling agent, c) placing the gelled particles obtained in contact with an alkaline aqueous solution to initiate a transacylation reaction at least at the surface of the gelled particles between the esterified polysaccharide and the polyamine contained in said particles, during a predetermined period of time sufficient to form a membrane on at least an outer surface of said particles, by a transacylation reaction with formation of covalent bonds between the esterified polysaccharide and the polyamine, d) adding an acidic agent to the reaction medium to substantially neutralize said particles thereby obtaining stabilized particles at least at the surface the membrane and e) recovering said neutralized and stabilized particles.

25. The process of claim 24, comprising generating drops of said first initial aqueous gellable solution.

26. The process of claim 25, further comprising preparing an aqueous or hydrophobic liquid phase to be encapsulated and performing a coextrusion through an extrusion nozzle having an external annular orifice and an internal central orifice by feeding said first initial aqueous gellable solution into said external annular orifice and said aqueous or hydrophobic liquid phase to be encapsulated in said internal central orifice, under conditions resulting in the formation of individual drops comprising an external layer of said first initial aqueous gellable solution and an internal encapsulated layer of said aqueous or hydrophobic liquid phase to be encapsulated.

27. The process of claim 26, wherein said liquid phase to be encapsulated is an aqueous phase which contains a material selected from the group of a living material, a living animal cell, a living plant cell, a living animal tissue, a living plant tissue and a biological substance.

28. The process of claim 24, wherein a polyamine is added to the alkaline aqueous solution initiating the transacylation reaction.

29. The process of claim 24, wherein said gelling agent is selected from the group consisting of a monocation, a polyvalent cation, an aqueous solution of pH above 6.2 and a polyphosphate solution.

30. The process of claim 29, wherein said monovalent cation is potassium and said polyvalent cation is selected from the group consisting of calcium cation, iron cation, aluminium cation, copper cation, manganese cation and barium cation.

31. The process of claim 30, wherein the concentration of gelling agent in the aqueous solution forming the gelling bath ranges between 0.8M and 1M.

32. The process of claim 24, wherein the contacting time of the particles in the gelling bath ranges between 1 and 40 minutes.

33. The process of claim 24, wherein the concentration of gellable polysaccharide in the initial aqueous gellable solution ranges between 0.5% and 2%.

34. The process of claim 24, wherein the concentration of esterified polysaccharide in the initial aqueous gellable solution ranges between 0.5% and 20% by weight.

35. The process of claim 34, wherein the concentration of esterified polysaccharide in the initial aqueous gellable solution is of about 2% per weight.

36. The process of claim 24, wherein the concentration of polyamine in the initial aqueous gellable solution ranges between 1% and 30% by weight.

37. The process of claim 24, wherein the alkaline solution triggering the transacylation reaction has a pH ranging between 8 and 14.

38. The process of claim 24, wherein the alkaline solution triggering the transacylation reaction has a pH ranging between 10.5 and 12.5.

39. The process of claim 24, wherein said alkaline solution is obtained by addition of an alkaline agent selected from the group consisting of sodium hydroxide, potassium hydroxide, aqueous ammonia, an amine, triethanolamine, triethylamine and polyethyleneimine.

40. The process of claim 24, wherein the contacting time of the particles in the alkaline solution ranges between 5 min and 1 hour.

41. The process of claim 24, wherein said acidic agent is selected from the group consisting of a monocarboxylic organic acid, a polycarboxylic organic acid, a monocarboxylic organic acid having an alcohol function, a polycarboxylic organic acid having an alcohol function and in inorganic acid.

42. The process of claim 41, wherein said organic acid is selected from the group consisting of acetic acid, citric acid, tartaric acid, succinic acid, malic acid and lactic acid.

43. The process of claim 41, wherein said inorganic acid is selected from the group consisting of hydrochloric acid and sulfuric acid.

44. The process of claim 24, further comprising liquefying the particle contents after formation of said membrane by the transacylation reaction, by contacting said particles with a liquefying agent.

45. The process of claim 44, wherein said liquefying agent is selected from the group consisting of an aqueous citrate solution and an aqueous phosphate solution.

46. The process of claim 45, wherein the concentration of citrate or of phosphate ranges between 0.01M and 1M.

47. The process of claim 24, wherein said particles are dried.

48. The process of claim 47, wherein said particles are dried by freeze-drying, spraying in a gas heated to a drying temperature, or drying in a fluidized bed dryer.

49. A composition selected from the group consisting of a cosmetic, a pharmaceutical, a therapeutic, a food, an enzymatic composition, a composition for cell therapy, a composition for enzyme therapy, a composition for blood purification, a composition for reagents, a composition for toxicological tests in vitro, a composition for agriculture, a composition for coated seeds, a composition for biotechnological production containing particles comprising at least one esterified polysaccharide and at least one polyamine, and further a gellable polysaccharide when neither the esterified polysaccharide nor the polyamine are gellable under the conditions used for preparing said particle, said particle comprising, at least an outer membrane formed by a transacylation reaction with formation of covalent amide bonds between the esterified polysaccharide and the polyamine.

* * * * *